US010087220B2

(12) United States Patent
Aguera et al.

(10) Patent No.: US 10,087,220 B2
(45) Date of Patent: Oct. 2, 2018

(54) HUMAN ULIP/CRMP PROTEIN AND USE THEREOF IN DIAGNOSIS AND TREATMENT OF CANCERS AND PARANEOPLASTIC NEUROLOGICAL SYNDROMES

(71) Applicant: INSTITUT NATIONAL DE LA SANTA ET DE LA RECHERCHE MEDICALE (INSERM), Paris (FR)

(72) Inventors: Michele Aguera, Caluire (FR); Jean-Christophe Antoine, Chalain le Comtal (FR); Marie-Francoise Belin, Lyons (FR); Jerome Honnorat, Bron (FR); Veronique Rogemond, Lyons (FR)

(73) Assignee: INSTITUT NATIONAL DE LA SANTA ET DE LA RECHERCHE MEDICALE (INSERM), Paris (FR)

( * ) Notice: Subject to any disclaimer, the term of this patent is extended or adjusted under 35 U.S.C. 154(b) by 0 days.

(21) Appl. No.: 13/741,876

(22) Filed: Jan. 15, 2013

(65) Prior Publication Data

US 2013/0243755 A1   Sep. 19, 2013

Related U.S. Application Data

(62) Division of application No. 12/068,686, filed on Feb. 11, 2008, now Pat. No. 8,377,645, which is a division of application No. 10/220,042, filed as application No. PCT/FR01/00589 on Feb. 28, 2001, now Pat. No. 7,329,499.

(30) Foreign Application Priority Data

Feb. 29, 2000  (FR) ..................................... 00 02566
Apr. 18, 2000  (FR) ..................................... 00 05005

(51) Int. Cl.
| | | |
|---|---|---|
| C07K 14/705 | (2006.01) | |
| C07K 14/47 | (2006.01) | |
| C07K 14/435 | (2006.01) | |
| C07K 16/18 | (2006.01) | |
| G01N 33/68 | (2006.01) | |
| A61K 38/00 | (2006.01) | |

(52) U.S. Cl.
CPC ............ *C07K 14/47* (2013.01); *C07K 14/435* (2013.01); *C07K 14/4713* (2013.01); *C07K 14/4748* (2013.01); *C07K 14/705* (2013.01); *C07K 16/18* (2013.01); *G01N 33/6854* (2013.01); *A61K 38/00* (2013.01)

(58) Field of Classification Search
CPC .. C07K 14/4713; C07K 14/475; C07K 14/47; C07K 14/705; C07K 16/18; A61K 38/1709
See application file for complete search history.

(56) References Cited

U.S. PATENT DOCUMENTS

2005/0175607 A1 *  8/2005  Tang ..................... C07K 14/47
                                                          424/145.1

FOREIGN PATENT DOCUMENTS

WO        WO 01/64834 A2 *  9/2001

OTHER PUBLICATIONS

Overview of ELISA, ThermoFisher Scientific, 6 pages, undated, but available at https://www.thermofisher.com/us/en/home/life-science/protein-biology/protein-biology-learning-center/protein-biology-resource-library/pierce-protein-methods/overview-elisa.html.
Mahmood, et al., "Western Blot: Technique, Theory and Trouble Shooting", Sep. 2012, pp. 429-434, vol. 4, No. 9, N Am J Med Sci.

* cited by examiner

*Primary Examiner* — Robert C Hayes
(74) *Attorney, Agent, or Firm* — B. Aaron Schulman, Esq.; Stites & Harbison, PLLC

(57) ABSTRACT

A purified polypeptide, designated ULIP6, comprising the amino acid sequence SEQ ID No. 2 or an epitopic fragment of said polypeptide, comprising the sequence SEQ ID No. 4, is provided along with its nucleic acid sequences. In addition, antibodies to the polypeptide and methods of diagnosing paraneoplastic neurological syndromes and/or for the early diagnosis of the formation of cancerous tumors are also provided.

Figure 1:
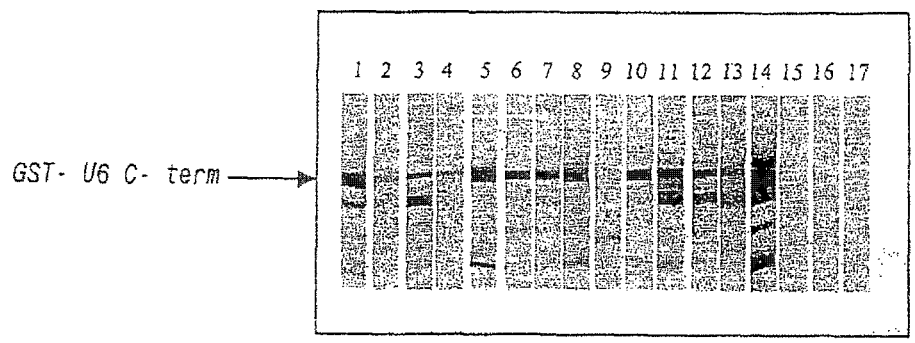

3 Claims, 1 Drawing Sheet
Specification includes a Sequence Listing.

HUMAN ULIP/CRMP PROTEIN AND USE THEREOF IN DIAGNOSIS AND TREATMENT OF CANCERS AND PARANEOPLASTIC NEUROLOGICAL SYNDROMES

CROSS REFERENCE TO RELATED APPLICATIONS

The present invention is a divisional application of U.S. application Ser. No. 12/068,686, filed Feb. 11, 2008, which is a divisional of U.S. application Ser. No. 10/220,042, filed Nov. 19, 2002 which is a 371 application of PCT/FR01/00589, filed Feb. 28, 2001, all of said applications incorporated herein by reference.

FIELD OF THE INVENTION

The invention relates to a novel human ULIP/CRMP protein and to the use thereof in diagnosis and treatment of cancers and paraneoplastic neurological syndromes.

BACKGROUND OF THE INVENTION

Paraneoplastic neurological syndromes (PNSs) occur in the instance of a cancer, often before its discovery, and are not connected to either the tumor proliferation itself (direct invasion, metastases) or the treatment. Their frequency is estimated to be, overall, approximately 1% of cancers. Several clinical pictures have been individualized for a long time (encephalomyelitis, Denny-Brown sensory neuropathy, cerebella atrophy, limbic encephalitis, opsoclonus, etc.) corresponding in fact to the either elective or preferential attack of certain groups of neurons. The frequency of inflammatory cells in the vicinity of the lesions for many years brought to mind the possibility of an autoimmune or viral process. The more recent demonstration of autoantibodies in the serum and in the cerebrospinal fluid (CSF) of patients suffering from PNS, specific for the type of tumor and for the type of neurons which degenerate, has revived the hypothesis that autoimmunity contributes to generating this pathological condition (Graus et al., 1985; Greenlee et al., 1983).

Besides the presence of a high titer of these antibodies in the blood and the CSF of patients, there are several arguments suggesting that PNSs are the product of autoimmune mechanisms. Thus, the antigens recognized in the central nervous system are also present in the tumors of patients (Anderson et al., 1987). Antibodies specifically directed against these antigens and also B and T lymphocytes are found within the tumor tissue (Hetzel et al., 1990).

These data suggest that the autoimmune process could be triggered by the expression of tumor antigens. A crossed immunity process could cause the lesions in the central nervous system. Other arguments also indicate that the cerebral lesions result from the autoimmune response. Thus, in the brain of the patients, the specific antibody titer is higher than that of the serum and of the CSF (Dalmau et al., 1991). In addition, in the case of encephalomyelitis associated with anti-Hu antibodies, there is an intense lymphocytic reaction, made up of B and T cells, located in proximity to neurons undergoing destruction (Dalmau et al., 1991; Graus et al., 1990).

Several types of autoantibody allowing precise syndromic groupings as a function of immunological, neurological and cancer-related criteria have been described.

Thus, anti-Yo antibodies are found in the serum and the CSF of women having paraneoplastic cerebella atrophy and a gynecological cancer (ovary, breast or uterus) (Greenlee et al., 1983; Jaeckle et al., 1985).

These antibodies recognize two cytoplasmic proteins, of 34 and 62 kDa, specific for Purkinje cells of the cerebellum.

Anti-Ri antibodies are found in the serum and the CSF of patients (mainly women) having opsomyoclonus, a cerebella syndrome and breast cancer. These antibodies recognize two proteins, of 50 and 80 kDa, specific for central nervous system neurons (Luque et al., 1991).

Anti-Hu antibodies are most commonly encountered in the course of PNSs. They are found in the serum and the CSF of patients having Denny-Brown's syndrome or encephalomyeloneuritis and small-cell lung cancer (Graus et al., 1985; Dalmau et al., 1992). These autoantibodies recognize several proteins, of 37 to 45 kDa, expressed specifically by all the neurons of the nervous system.

Another type of autoantibody has been identified in patients having PNS: anti-CV2 antibodies (Antoine et al., 1993; Honnorat et al., 1996). The latter are atypical, in the sense that the antigenic target recognized in adulthood is essentially non-neuronal, although post-mortem analysis of the brain of four patients makes it possible to observe neuronal loss, gliosis and an inflammatory process characteristic of PNSs.

The originality of the discovery of these autoantibodies lies, firstly, in their demonstration. The latter had evaded all the usual investigations which consisted in revealing the antigens recognized, by immunohistochemistry on post-mortem brain. The antigen recognized is in fact soluble and disappears from post-mortem brain under the majority of conditions for fixing. Only fixing of human post-mortem tissue by immersion in paraformaldehyde, or fixing in situ by perfusion of paraformaldehyde in animals, has made it possible to reveal the presence of these antibodies in the CSF or the serum of patients suffering from PNS (Antoine et al., 1993; Honnorat et al., 1996).

The anti-CV2 autoantibodies present in the sera of patients suffering from paraneoplastic neurological syndrome (PNS) have been defined by their ability to recognize, by indirect immunohistochemistry, a cytoplasmic antigen expressed specifically, in adult rat brain, by a subpopulation of oligodendrocytes of the brain stem, of the medulla and of the cerebellum.

The originality of these autoantibodies lies, secondly, in their diagnostic value. Their presence in the serum or the CSF of patients is of diagnostic value since it makes it possible to specify the paraneoplastic origin of a neurological syndrome. The discovery of these antibodies, when it precedes that of cancer, directs the search for this cancer and enables it to be discovered. Such was the case for six patients out of 19 having anti-CV2 antibodies. The clinical disorders were different depending on the patients, some of them exhibiting a picture of limbic encephalitis, others encephalomyeloneuritis and others Lambert-Eaton syndrome. Nevertheless, in more than 60% of cases, the cerebella syndrome was predominant. The most commonly associated tumor was small-cell lung cancer (60% of cases).

Experiments on newborn rat brains have shown that these anti-CV2 antibodies react with a 66 kDa protein (Honnorat et al., 1996).

In adult brain, this antigen is located in a subpopulation of oligodendrocytes or in cells which retain differentiation capacities in the adult brain (olfactory bulb, dentate gyrus). The antigen recognized is thought to play a role in neuronal survival, via neuron/oligodendrocyte interactions, as suggested by the loss of neurons observed in the post-mortem brain of patients suffering from PNS.

It's very restricted expression in adulthood contrasts with very strong and transient expression in the central and peripheral nervous system in development, suggesting the probable role of this antigen in the development of the nervous system.

In application WO 98/37192 and the article by Honnorat et al. from 1999, the target antigen of the anti-CV2 autoantibodies, which corresponds to a protein designated "POP-66" for "paraneoplastic oligodendrocyte protein 66 kDa", was identified as being the human form of the ULIP-4 protein. The ULIP (for "Unc-33 like phosphoprotein") proteins are involved in the control of neuronal development and axonal transport (Byk et al., 1996). Four members of this family had been identified by three different teams (Byk et al., 1998, Wang and Strittmatter, 1996; and Hamajima et al., 1996). A thorough search for possible other members of this family had come to nothing.

The authors of the present invention were then confronted with new results, which were not coherent with the identification established by application WO 98/37192; although all the anti-CV2 sera tested on Hela cells unquestionably recognized the recombinant ULIP 4 protein in immunohistochemistry, only 20% of these sera recognized the ULIP 4 protein by Western blotting on these same cell extracts. Now, all the anti-CV2 sera tested recognized, moreover, by Western blotting, the same 66 kDa protein after immunoprecipitation, on brain extracts. In addition, the ULIP4 mRNA was only very weakly expressed in oligodendrocytes by in situ hybridization. Based on these data, the authors of the present invention supposed that a new member of the ULIP family, unidentified to date, strongly expressed by oligodendrocytes and recognized in Western blotting by all the anti-CV2 sera, could exist.

SUMMARY OF THE INVENTION

The authors of the present invention have now demonstrated that, contrary to what was proposed by application WO 96/37192, POP-66, the major target antigen of the anti-CV2 autoantibodies, is not the ULIP 4 protein but another protein. They have succeeded in characterizing this protein. It is a novel human protein of the ULIP family, designated ULIP6.

ULIP 6 comprises, in its C-terminal portion, a major epitope recognized by anti-CV2 antibodies in Western blotting.

A subject of the present invention is therefore a purified ULIP 6 polypeptide comprising the amino acid sequence SEQ ID No. 2.

An epitopic fragment of the polypeptide mentioned above, comprising the sequence SEQ ID No. 4, is also included in the present invention. More particularly, a subject of the invention is the purified peptide of sequence SEQ ID No. 4.

A subject of the present invention is also an isolated nucleic acid encoding the ULIP6 polypeptide as defined above, preferably comprising the nucleotide sequence SEQ ID No. 1. The sequence SEQ ID No. 1 has a 5' noncoding region (nucleotides 1 to 162), an open reading frame (nucleotides 163 to 1854) and a 3' noncoding region (nucleotides 1855 to 3074).

A subject of the present invention is also an isolated nucleic acid comprising the nucleotide sequence SEQ ID No. 3, which corresponds to the noncoding region in 3' of the human coding sequence SEQ ID No. 1. This noncoding sequence, as well as the 5' noncoding portion (nucleotides 1 to 162 of SEQ ID No. 1), may in particular be used for preparing specific probes.

BRIEF DESCRIPTION OF THE DRAWING FIGURES

FIG. 1 represents a Western blot performed on protein extracts of E. coli expressing the fusion protein GST-ULIP6 C-term. These extracts were separated by SDS-12.5% PAGE, transferred onto a PVDF membrane and incubated with human sera. Lanes 1 to 14: anti-CV2 sera; lanes 15 to 17: control sera.

Figure 2:
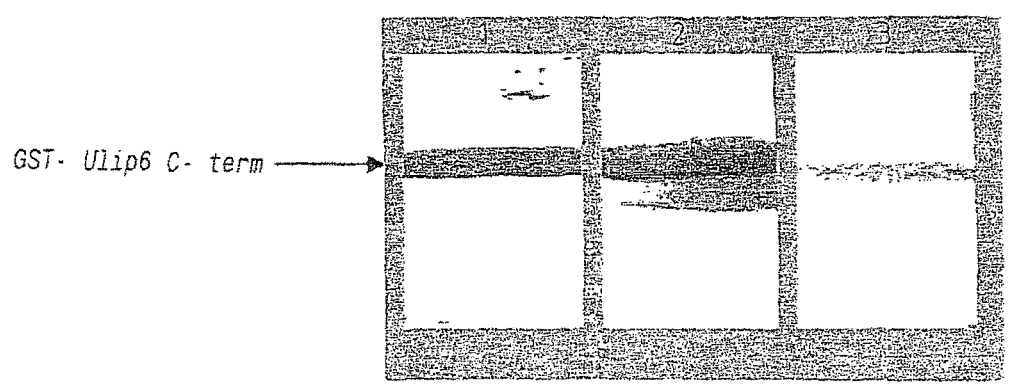

FIG. 2 represents a Western blot performed on GST-ULIP6 C-term fusion proteins after purification on agarose-glutathione beads. The protein is recognized by two anti-CV2 sera (lane 1: serum 94-822, lane 2: serum 95-590) but not by a control serum (lane 3).

DETAILED DESCRIPTION OF THE PREFERRED EMBODIMENTS

The polypeptide of the present invention may be synthesized by all the methods well known to those skilled in the art. The polypeptide of the invention may, for example, be synthesized by synthetic chemistry techniques, such as synthesis of the Merrifield type, which is advantageous for reasons of purity, of antigenic specificity and of lack of unwanted by-products, and for its ease of production.

A recombinant ULIP6 protein can also be produced using a method in which a vector containing a nucleic acid comprising the sequence SEQ ID No. 1 is transferred into a host cell, which is cultured under conditions which allow expression of the corresponding polypeptide.

The protein produced can then be recovered and purified.

The purification methods used are known to those skilled in the art. The recombinant polypeptide obtained can be purified from cell lysates and extracts, and from the culture medium supernatant, using methods employed individually or in combination, such as fractionation, chromatography methods, immunoaffinity techniques using specific mono- or polyclonal antibodies, etc.

The nucleic acid sequence of interest, encoding the ULIP6 polypeptide, may be inserted into an expression vector, in which it is functionally linked to elements for regulating its expression, such as in particular transcription promoters, activators and/or terminators.

The signals controlling the expression of the nucleotide sequences (promoters, activators, termination sequences, etc.) are chosen as a function of the cellular host used. To this effect, the nucleotide sequences according to the invention may be inserted into vectors which replicate autonomously in the chosen host, or vectors which integrate in the chosen host. Such vectors will be prepared according to the methods commonly used by those skilled in the art, and the clones resulting therefrom can be introduced into a suitable host using standard methods, such as, for example, electroporation or calcium phosphate precipitation.

The cloning and/or expression vectors as described above, containing a nucleotide sequence defined according to the invention, are also part of the present invention.

The invention is also directed toward the host cells transfected, transiently or stably, with these expression vectors. These cells can be obtained by introducing into host cells a nucleotide sequence inserted into a vector as defined above, and then culturing said cells under conditions which allow replication and/or expression of the transfected nucleotide sequence.

The cellular host may be chosen from prokaryotic systems, such as bacteria, or eukaryotic systems, such as, for example, yeasts, insect cells, CHO cells (Chinese hamster ovary cells) or any other system advantageously available. A preferred cellular host for expressing the proteins of the invention consists of the bacterium *E. coli*.

The nucleotide sequences of the invention may or may not be of artificial origin. They may be DNA or RNA sequences obtained by screening sequence libraries using probes developed on the basis of the sequence SEQ ID No. 1 or 3. Such libraries may be prepared by conventional molecular biology techniques known to those skilled in the art.

The nucleotide sequences according to the invention may also be prepared by chemical synthesis, or else by mixed methods which include chemical or enzymatic modification of sequences obtained by screening libraries.

This nucleic acid makes it possible to prepare nucleotide probes capable of hybridizing strongly and specifically with a nucleic acid sequence, a genomic DNA sequence or a messenger RNA sequence, encoding a polypeptide according to the invention or a biologically active fragment thereof. Suitable hybridization conditions correspond to the temperature and ionic strength conditions usually used by those skilled in the art (Sambrook et al., 1989), preferably to temperature conditions of between ($T_m$ minus 5° C.) and ($T_m$ minus 30° C.) and even more preferably to temperature conditions of between ($T_m$ minus 5° C.) and ($T_m$ minus 10° C.) (high stringency), Tm being the theoretical melting temperature, defined as being the temperature at which 50% of the paired strands separate. Such probes are also part of the invention. They may be used as a diagnostic tool in vitro for detecting, via hybridization experiments, transcripts specific for the polypeptides of the invention in biological samples, or for demonstrating aberrant syntheses or genetic abnormalities resulting from a polymorphism, from mutations or from incorrect splicing.

The probes of the invention comprise a minimum of 10 nucleotides, and as a maximum comprise all of a nucleotide sequence SEQ ID No. 1 or 3, or of the strand complementary thereto.

The nucleic acid of the invention may also be used to prepare oligonucleotide primers which hybridize, under high stringency conditions, to the sequence SEQ ID No. 1 or 3.

These sense and/or antisense oligonucleotide primers may be of use for sequencing reactions or specific amplification reactions according to the "PCR" (polymerization chain reaction) technique or any other variant thereof.

Preferentially, the probes or primers of the invention are labeled prior to their use. For this, several techniques are within the scope of those skilled in the art, such as, for example, fluorescent, radioactive, chemiluminescent or enzymatic labeling.

The methods for diagnosis in vitro in which these nucleotide probes are used for detecting aberrant syntheses or genetic abnormalities, such as loss of heterozygosity and genetic rearrangement, in the nucleic acid sequences encoding a ULIP6 polypeptide according to the invention, are included in the present invention. Such a type of method comprises:

contacting a nucleotide probe of the invention with a biological sample under conditions which allow the formation of a hybridization complex between said probe and the abovementioned nucleotide sequence, optionally after a prior step of amplification of the abovementioned nucleotide sequence;
detecting the hybridization complex possibly formed;
optionally sequencing the nucleotide sequence which forms the hybridization complex with the probe of the invention.

The probes of the invention can also advantageously be used for detecting chromosomal abnormalities.

The nucleotide sequences according to the invention are, moreover, useful in the therapeutic field, for preparing antisense sequences capable of hybridizing specifically with a nucleic acid sequence, including a messenger RNA, which can be used in gene therapy. A subject of the invention is thus antisense sequences capable of inhibiting, at least partially, the production of a polypeptide according to the invention, as defined above.

They are of more particular use in the treatment of disorders of the central and peripheral nervous system and of vision, in particular in the treatment of paraneoplastic neurological syndromes, and also in anticancer treatment, in particular for tumors associated with paraneoplastic neurological syndromes.

The exploitation of the ULIP proteins, and in particular ULIP6, and also of the antibodies directed against these proteins, is promising in various fields.

Thus, detection of the anti-CV2 autoantibody by immunofluorescence on fixed animal brain is currently used as a diagnostic test.

The production of recombinant ULIP6 protein according to the invention makes it possible to produce a rapid and reliable test (of the Elisa or Western blotting type) for detecting anti-CV2 antibodies.

Such tests already exist for anti-Hu, anti-Yo and anti-Ri antibodies. The test for detecting anti-CV2s in the serum of patients could be prescribed in the case of suspicion of paraneoplastic neurological syndrome and would, consequently, include anti-CV2 antibodies as well as the other antibodies identified in PNSs as mentioned above.

The invention is therefore also directed toward a method for the diagnosis of paraneoplastic neurological syndromes and/or for the early diagnosis of the formation of tumors of cancerous origin, wherein antibodies directed against a ULIP6 protein are demonstrated in a biological sample (such as blood, serum, CSF, etc.) taken from an individual, by contacting a biological sample taken from an individual with a purified ULIP6 polypeptide optionally attached to a support, under conditions which allow the formation of specific immunocomplexes between said polypeptide and the autoantibodies possibly present in the biological sample, and
detecting the specific immunocomplexes possibly formed.

A subject of the invention is therefore a composition useful for the diagnosis of paraneoplastic neurological syndromes and/or for the early diagnosis of the formation of tumors, that comprises a ULIP6 polypeptide or an epitopic fragment of said polypeptide.

Advantageously, instead of the complete polypeptide, the C-terminal portion comprising the dominant epitope (for example the fragment ranging from amino acid No. 475 to amino acid 564) may be used. An epitopic fragment of the ULIP6 polypeptide, comprising the sequence SEQ ID No. 4, may in particular be used. The peptide of sequence SEQ ID No. 4 has thus made it possible to produce antibodies which are very specific for ULIP6.

A subject of the invention is also a kit for the diagnosis of paraneoplastic neurological syndromes and for the early diagnosis of the formation of tumors, using a biological specimen, comprising:

at least one purified ULIP6 polypeptide, optionally attached to a support, means for revealing the formation of specific antigen/antibody complexes between an anti-ULIP6 autoantibody and said purified ULIP6 polypeptide, or polypeptide derivative or fragment, and/or means for quantifying these complexes.

A subject of the invention is also the mono- or polyclonal antibodies or fragments, chimeric antibodies or immunoconjugates thereof, obtained using a purified ULIP polypeptide or peptide comprising an amino acid sequence SEQ ID No. 2 or No. 4, and use thereof, for purifying or detecting a ULIP protein in a biological sample.

Polyclonal antibodies may be obtained from the serum of an animal immunized against the protein, produced, for example, by genetic recombination following the method described above, according to usual procedures.

The monoclonal antibodies may be obtained according to the conventional method of culturing hybridomas described by Köhler and Milstein.

The antibodies may be chimeric antibodies, humanized antibodies, and Fab and F(ab')2 fragments. They may also be in the form of immunoconjugates or of labeled antibodies.

The invention also relates to the use of antibodies directed against the ULIP6 protein, for demonstrating a ULIP6 protein in neoplasms and paraneoplastic neurological syndromes, for diagnostic purposes.

Preferentially, the invention relates to the use of monoclonal antibodies obtained from the polyclonal anti-CV2 serum of patients by immortalization of lymphocytes, according to the usual techniques known to those skilled in the art.

Thus, the antibodies directed against a protein of the ULIP family are of use for detecting abnormal expression of ULIP protein in patients having neurological syndromes, in whom no cancer has been diagnosed using conventional methods. This abnormal expression of ULIP6 protein may be correlated with the existence of a cancer which had not been detected. Thus, the antibodies directed against the ULIP6 protein are of use for the early diagnosis of a cancer.

Human or nonhuman antibodies, obtained from patients or obtained after immunization with all or part of the ULIP6 protein, as defined above, may also be labeled in a detectable manner, for example by association with a radioactive element, and may be injected into an individual. Using imaging processes well known to those skilled in the art, they may make it possible to detect or diagnose a cancerous tumor after antigenic reaction of these antibodies with the cells of the tumor.

A subject of the invention is therefore also a method for detecting or diagnosing a cancerous tumor, comprising the administration to a patient of an antibody as defined above, labeled in a detectable manner, and the visualization by imaging of the site of attachment of this antibody.

A subject of the invention is also a pharmaceutical composition comprising at least one therapeutic agent chosen from a purified ULIP6 protein, or a nucleic acid encoding said protein, an antisense sequence capable of hybridizing specifically with a nucleotide sequence SEQ ID No. 1 or No. 3, or an antibody directed against said protein, combined with a pharmaceutically acceptable vehicle.

The invention preferentially comprises pharmaceutical compositions comprising, as active principle, a purified ULIP6 polypeptide, preferentially in soluble form, combined with a pharmaceutically acceptable vehicle.

Such compositions offer a novel approach for treating disorders of the central and peripheral nervous system and of vision, and in particular paraneoplastic neurological syndromes. Moreover, they are of use for treating neurological disorders linked to neuronal loss and/or underexpression of the ULIP6 protein in the nervous system.

Thus, ULIP6 also proves to be of value in neurodegenerative pathological conditions, such as multisystemic atrophies which are disorders similar to those of PNSs and for which an abnormality of an oligodendrocytic subpopulation has been detected (Papp et al., 1992).

The compositions according to the invention are, moreover, of use in anticancer treatment.

The antibodies directed against the ULIP6 protein may be combined with antineoplastic agents, thus allowing targeting of the medicinal products to the tumor cells.

They may also be combined with a hydrophilic chemical group chosen so as to cross or so as not to cross the blood-brain barrier, depending on the type of tumor.

The ULIP6 protein and also the nucleotide sequences described above, and the antisense sequences or oligonucleotides, may be of use in the treatment of any type of cancer in which a gene encoding the ULIP6 protein is involved. Among examples of cancers, mention may be made of peripheral tumors, such as small-cell lung cancer, thymoma, breast cancer and ovarian cancer, and also brain tumors, preferably primary brain tumors of glial origin. The expression of ULIP6 in the nonproliferative cells of normal brain, its absence in normal tissues, such as lung or thymus, for example, its differential reexpression during tumorigenesis in these tissues, and the modulation of its expression in a tumor line during differentiation suggest, in this regard, that ULIP 6 may be a tumor suppressor gene.

A compound or a mixture of compounds of synthetic or natural origin, which inhibits the action of ULIP 6, may also be used.

Alternatively, stimulation of ULIP 6 may be desired. A compound or a mixture of compounds of synthetic or natural origin which activates the expression or the action of the ULIP 6 protein may then be used.

These activating or inhibiting compounds may be included in pharmaceutical compositions.

Preferentially, the pharmaceutical compositions according to the invention may be administered systemically, preferably intravenously, intramuscularly, intradermally or orally.

Their optimal methods of administration, dosages and pharmaceutical forms may be determined according to the criteria generally taken into account in establishing a therapeutic treatment suitable for a patient, such as, for example, the age or bodyweight of the patient, the seriousness of his or her general condition, the tolerance to the treatment and the side effects observed, etc.

The invention also comprises the use of a purified ULIP6 protein, a nucleic acid encoding said protein or belonging to the noncoding regions of the ULIP6 gene, an antisense sequence capable of hybridizing specifically with a nucleotide sequence SEQ ID No. 1 or No. 3, or an antibody directed against said protein, combined with a pharmaceutically acceptable vehicle, for manufacturing a medicament intended to treat neurodegenerative diseases and neoplasms.

Finally, a subject of the invention is a method for treating neurodegenerative diseases and neoplasms, comprising the administration of a therapeutically effective amount of a pharmaceutical composition as defined above to an individual requiring such a treatment.

The examples and figures, for which the legends are presented below, are given by way of illustration.

Example 1: Identification of the Target for Anti-CV2 Antibodies

After expression of the recombinant proteins of the Ulip family in HeLa cells, the authors of the invention were able to show that the anti-CV2 sera then in their possession all recognized Ulip4 by immunohistochemistry. This result would suggest that Ulip4 could be the major antigen recognized by the anti-CV2 sera (Honnorat et al., 1999). On the other hand, when a larger group of sera was tested by Western blotting on the Ulip4 protein expressed in *E. coli*, they noticed that while several anti-CV2 sera unquestionably recognized the recombinant Ulip4 protein, some did not recognize it, although all the anti-CV2 sera recognized, by Western blotting, the same 66 kDa protein after immunoprecipitation of protein extracts from brains (Honnorat et al., 1996). In addition, by in situ hybridization, the oligodendrocytes did not express the Ulip4 messenger RNA. The authors of the invention then put forward the hypothesis of the existence of another protein homologous to the Ulip proteins, which had not yet been described, and which was expressed by oligodendrocytes.

In order to search for this protein, an anti-CV2 serum, which did not recognize recombinant Ulip4 by Western blotting, was used to screen an expression library. A cDNA library of human spinal cord, the site of maximum expression of the CV2 antigen in adults, cloned into the lambda gt11 phage was chosen (Clontech, Palo Alto, USA). The phages were screened at a density of $2 \times 10^4$ pfu per 150 mm-diameter dish. After incubation for 3 hours 30 minutes at 42° C., the dishes were covered with a nitrocellulose membrane incubated in IPTG (10 mM), and reincubated for 3 hours at 37° C. The membranes were then saturated in PBS-Tween-skimmed milk, and then incubated overnight with the serum diluted to 1/100. The membranes were then washed in PBS-Tween and then incubated with a peroxidase-labeled anti-human immunoglobulin antiserum. After washing, the membranes were revealed by the diaminobenzidine method. The clones giving a positive signal were purified by successive subculturing until 100% of positive clones was obtained. Four cDNAs of 1400 to 1700 base pairs and encoding the C-terminal portion of the same protein were identified. The clone having the largest coding sequence (clone 97) contained 1490 base pairs (nucleotides 1585 to 3074 of sequence ID No. 1) with an open reading frame of 270 nucleotides encoding a 90 amino acid polypeptide (amino acids 475 to 564 of sequence ID No. 2). After a homology search in databanks, it was noted that this polypeptide (named in the remainder of the study Ulip6 C-Term) exhibited a homology of 35% with the C-terminal portion of each of the already known members of the Ulip family, and that no homology existed with other protein families.

Example 2: Production of the Recombinant Protein GST-ULIP6 C-Term

To confirm that this polypeptide was indeed the antigen recognized by the anti-CV2 sera, the coding phase of clone 97 was cloned into a bacterial expression vector, pGex 2T (Pharmacia Amersham Biotech, Sweden). This vector allows expression, in *E. coli*, of the protein of interest as a fusion with glutathione-S-transferase (GST, 26 kDa). By Western blotting, 16 of the 18 anti-CV2 sera tested recognized the GST-Ulip6-CTerm fusion protein in a bacterial protein extract, i.e. 89% positives (FIG. 1). It should be noted that the Ulip6 C-Term polypeptide has a molecular weight of 10 kDa, which represents approximately 15% of a 66 kDa protein. None of these sera recognized GST alone. 100 control sera were also tested. None showed any reactivity with respect to the GST-Ulip6 C-Term fusion protein. With the aim of having as specific a test as possible, the authors of the invention also tested the anti-CV2 sera on the GST-Ulip6 C-Term fusion protein purified on agarose-glutathione beads. FIG. 2 shows an example of the results obtained by Western blotting.

Example 3: Northern Blotting on Human Spinal Cord RNA

To determine the size of the transcript of the Ulip6 gene, a Northern blotting analysis was carried out on purified polyA+ RNAs extracted from human spinal cord (Clontech, Palo Alto, USA). The probe corresponded to the entire clone 97 labeled with alpha $^{32}$P dCTP. The RNAs were separated on a 1.2% agarose formaldehyde electrophoresis gel and transferred onto a nylon membrane. After prehybridization with the rapid hybridization solution (Clontech, Palo Alto, USA), the membrane was incubated with the probe for one hour. After washing, the membrane was exposed on a film overnight at −80° C. A single band corresponding to a 5 kb transcript was revealed.

Example 4: In Situ Hybridization on Spinal Cord

To verify the presence of the Ulip6 messenger RNA in oligodendrocytes, an in situ hybridization analysis was carried out on frontal sections of medulla. The probe used was a cold RNA probe obtained by transcription of clone 97 subcloned into pBluescript SK (Stratagene) and labeled with digoxigenin. A sense probe was used as negative control. Specific labeling of oligodendrocytes could be observed.

Example 5: Production of a Rabbit Anti-Ulip6 Antibody

Polyclonal antibodies were produced by immunizing rabbits against a peptide specific to the Ulip6 protein (peptide Pep Ulip6="KEMGTPLADTPTRPVTRHGG" of sequence SEQ ID No. 4, corresponding to amino acid fragment 505 to 524 on SEQ ID No. 2). The peptide was synthesized on a peptide synthesizer (432A Peptide Synthesizer SYNERGY, Applied Biosystems), by the company COVALAB (Lyon, France). The purity of the samples was controlled by HPLC and mass spectrometry. One milligram of peptide coupled to hemocyanine and with complete Freund's adjuvant was injected into rabbits (COVALAB, Lyon, France). Every 3 weeks, a further injection of 0.5 mg was given. The production of antibodies and their specificity were analyzed by Western blotting and immunohistochemistry, using preimmune sera as a control.

The antibodies obtained recognized the GST-Ulip6 C-Term protein by Western blotting, a 66 kDa protein on brain extracts, and specifically labeled oligodendrocytes by immunohistochemistry on rat medulla sections.

Example 6: Search for the Complete Ulip6 Sequence

In order to obtain a complete Ulip6 cDNA, the human spinal cord cDNA library, cloned into the lambda gt11 phage (Clontech, Palo Alto, USA), was screened with a radioactive probe. This probe, obtained by PCR, was labeled with alpha $^{32}$P dCTP, and corresponded to nucleotides 1585 to 1854 of the sequence ID No. 1. The phages were screened at a density of 2×10$^4$ pfu per 150 mm-diameter dish. After incubation for 6 hours at 37° C., a replica was obtained on a nylon membrane. This membrane was treated so as to denature the phages, and the DNA was then fixed overnight at 42° C. After prehybridization with the rapid hybridization solution (Clontech, Palo Alto, USA), the membrane was incubated for one hour with the radioactive probe. After washing, the membrane was exposed on a film overnight at −80° C. Clones giving a positive signal were purified by successive subculturing until 100% of positive clones was obtained. The largest cDNA obtained comprised 3074 nucleotides (SEQ ID No. 1) and comprised an open reading frame of 1692 nucleotides (nucleotides No. 163 to 1854 of SEQ ID No. 1). It encoded a 564 amino acid protein (SEQ ID No. 2), the C-terminal portion of which was strictly identical to the ULIP6 C-term polypeptide (amino acids 475 to 564 on SEQ ID No. 2). After alignment of the protein obtained with the four known human ULIP/CRMP proteins, 50% homology was observed.

BIBLIOGRAPHY

Anderson et al., CRC Crit. Rev. Neurobiol., 1987, vol. 3, pp 245-99

Antoine J. C. et al., Journal of the Neurological Sciences, 1993, vol. 117, pp 215-223

Byk et al., Journal of Neuroscience, 1996, vol. 16(2), pp 688-701

Byk T., Ozon S., Sobel A., (1998). Eur. J. Biochem, 254: 14-24

Dalmau et al., Neurology, 1991, vol. 41, pp 1757-64

Graus et al., Neurology, 1985, vol. 35, pp 538-543

Greenlee et al., Ann. Neurol., 1983, vol. 14, pp 609-13

Hamajima N., Matsuda K., Sakata S., Tamaki M., Nonaka M., (1996). Gene, 180:157-163

Hetzel et al., Mayo Clin. Proc., 1990, vol. 65, pp 1558-63

Honnorat J. et al., Journal of Neurology, Neurosurgery and Psychiatry, 1996, vol. 61, pp 270-278

Jaeckle et al., Ann. Neurol., 1985, vol. 18, pp 592-600

Köhler and Milstein, Nature, 1975, vol. 256, pp 495-497

Levy N., Mattel M. G., 1995, Geneprobs II, a practical approach, B. D. Hames and S. J. Higgins, Oxford University Press, pp 211-243

Luque et al., Ann. Neurol., 1991, vol. 29, pp 241-51

Sambrook et al., Molecular Cloning, a laboratory manual, 1989, 9.47-9.62

Wang L. H. and Strittmatter S. M., (1996). J. Neurosci., 16:6197-6207.

What is claimed is:

1. An epitopic fragment of a recombinant polypeptide, designated ULIP6, comprising the amino acid sequence SEQ ID No. 2, wherein the epitopic fragment comprises the sequence SEQ ID No. 4, and wherein the epitopic fragment is attached to a support, wherein the support is a support for use in ELISA or Western blotting.

2. A purified recombinant polypeptide, designated ULIP6, comprising the amino acid sequence SEQ ID No. 2 or a recombinant epitopic fragment of said recombinant polypeptide, comprising the sequence SEQ ID No. 4, wherein the purified recombinant polypeptide is detectably labeled with glutathione-S-transferase.

3. The epitopic fragment of claim 1, wherein the epitopic fragment can form an immunocomplex with anti-CV2 antibody that is detectable by Elisa or Western blotting.

* * * * *

SEQUENCE LISTING

```
<160> NUMBER OF SEQ ID NOS: 4

<210> SEQ ID NO 1
<211> LENGTH: 3074
<212> TYPE: DNA
<213> ORGANISM: Homo sapiens
<220> FEATURE:
<221> NAME/KEY: CDS
<222> LOCATION: (163)..(1854)
<223> OTHER INFORMATION:

<400> SEQUENCE: 1
cccgccccac tctggactcc cgcgctgggc gcgctgaggc ggcccccgag cgagcgcgcg      60
tgcagccgcc gccgccccga gcacccgcag ctccggcgcc gcggcgagac ggagacggac     120
cgagccacgg gcccccgcgg ccgcagcatc tcggaggaga ac atg ctt gcc aac       174
                                               Met Leu Ala Asn
                                                 1 tca gcc agc gtg agg atc ctc atc aag gga ggc aag gtg gtg aac gat     222
Ser Ala Ser Val Arg Ile Leu Ile Lys Gly Gly Lys Val Val Asn Asp
 5               10                  15                  20 gac tgc acc cac gag gct gac gtc tac atc gag aat ggc atc atc cag     270
Asp Cys Thr His Glu Ala Asp Val Tyr Ile Glu Asn Gly Ile Ile Gln
             25                  30                  35 cag gtg ggc cgc gag ctc atg atc cct ggc ggg gcc aag gtg att gat     318
Gln Val Gly Arg Glu Leu Met Ile Pro Gly Gly Ala Lys Val Ile Asp
         40                  45                  50 gcc aca gga aaa ctg gtg atc cct ggt ggc atc gac acc agc acc cac     366
Ala Thr Gly Lys Leu Val Ile Pro Gly Gly Ile Asp Thr Ser Thr His
     55                  60                  65 ttc cac cag acc ttc atg aat gcc acg tgc gtg gac gac ttc tac cat     414
Phe His Gln Thr Phe Met Asn Ala Thr Cys Val Asp Asp Phe Tyr His
 70                  75                  80 ggg acc aag gca gca ctc gtc gga ggc acc acc atg atc atc ggc cac     462
Gly Thr Lys Ala Ala Leu Val Gly Gly Thr Thr Met Ile Ile Gly His
 85                  90                  95                 100
```

-continued

| | |
|---|---|
| gtc ctg ccc gac aag gag acc tcc ctt gtg gac gct tat gag aag tgc<br>Val Leu Pro Asp Lys Glu Thr Ser Leu Val Asp Ala Tyr Glu Lys Cys<br>     105       110      115 | 510 |
| cga ggt ctg gcc gac ccc aag gtc tgc tgt gat tac gcc ctc cac gtg<br>Arg Gly Leu Ala Asp Pro Lys Val Cys Cys Asp Tyr Ala Leu His Val<br>  120       125       130 | 558 |
| ggg atc acc tgg tgg gca ccc aag gtg aaa gca gaa atg gag aca ctg<br>Gly Ile Thr Trp Trp Ala Pro Lys Val Lys Ala Glu Met Glu Thr Leu<br>    135        140      145 | 606 |
| gtg agg gag aag ggt gtc aac tcg ttc cag atg ttc atg acc tac aag<br>Val Arg Glu Lys Gly Val Asn Ser Phe Gln Met Phe Met Thr Tyr Lys<br>150        155        160 | 654 |
| gac ctg tac atg ctt cga gac agt gag ctg tac caa gtg ttg cac gct<br>Asp Leu Tyr Met Leu Arg Asp Ser Glu Leu Tyr Gln Val Leu His Ala<br>165        170       175       180 | 702 |
| tgc aag gac att ggg gca atc gcc cgc gtc cat gct gaa aat ggg gag<br>Cys Lys Asp Ile Gly Ala Ile Ala Arg Val His Ala Glu Asn Gly Glu<br>      185        190       195 | 750 |
| ctt gtg gcc gag ggt gct aag gag gca ctg gat ttg ggg atc aca ggc<br>Leu Val Ala Glu Gly Ala Lys Glu Ala Leu Asp Leu Gly Ile Thr Gly<br>    200        205       210 | 798 |
| cca gaa gga atc gag atc agc cgt cca gag gag ctg gaa gct gaa gcc<br>Pro Glu Gly Ile Glu Ile Ser Arg Pro Glu Glu Leu Glu Ala Glu Ala<br>    215        220       225 | 846 |
| act cat cgt gtt atc acc att gca aac agg act cac tgt cca atc tac<br>Thr His Arg Val Ile Thr Ile Ala Asn Arg Thr His Cys Pro Ile Tyr<br>  230       235       240 | 894 |
| ctg gtc aac gtg tcc agt atc tcg gct ggt gac gtt atc gca gct gct<br>Leu Val Asn Val Ser Ser Ile Ser Ala Gly Asp Val Ile Ala Ala Ala<br>245        250        255       260 | 942 |
| aag atg caa ggg aag gtt gtg ctg gcg gag acc acc gca cat gcc<br>Lys Met Gln Gly Lys Val Val Leu Ala Glu Thr Thr Ala His Ala<br>      265        270       275 | 990 |
| acg ctg aca ggc tta cac tac tac cac cag gac tgg tcc cac gcg gct<br>Thr Leu Thr Gly Leu His Tyr Tyr His Gln Asp Trp Ser His Ala Ala<br>    280        285       290 | 1038 |
| gcc tat gtc acg gtg cct ccc ctg aga ctg gac acc aac acc tca acc<br>Ala Tyr Val Thr Val Pro Pro Leu Arg Leu Asp Thr Asn Thr Ser Thr<br>      295        300       305 | 1086 |
| tac ctc atg agc ctg ctg gcc aat gac act ctg aac atc gtg gca tca<br>Tyr Leu Met Ser Leu Leu Ala Asn Asp Thr Leu Asn Ile Val Ala Ser<br>  310       315       320 | 1134 |
| gat cac cgg cct ttc acc aca aag cag aaa gct atg ggc aag gaa gac<br>Asp His Arg Pro Phe Thr Thr Lys Gln Lys Ala Met Gly Lys Glu Asp<br>325        330        335       340 | 1182 |
| ttc acc aag atc cca cat gga gtg agt ggc gtg cag gac cgc atg agc<br>Phe Thr Lys Ile Pro His Gly Val Ser Gly Val Gln Asp Arg Met Ser<br>      345        350       355 | 1230 |
| gtc atc tgg gag aga gga gtg gtt gga gga aag atg gat gag aac cgt<br>Val Ile Trp Glu Arg Gly Val Val Gly Gly Lys Met Asp Glu Asn Arg<br>    360        365       370 | 1278 |
| ttt gtg gcc gtt acc agt tcc aac gca gct aag ctt ctg aac ctg tat<br>Phe Val Ala Val Thr Ser Ser Asn Ala Ala Lys Leu Leu Asn Leu Tyr<br>    375        380       385 | 1326 |
| ccc cgc aag ggc cgc att att ccc gga gcc gat gct gat gtg gtg gtg<br>Pro Arg Lys Gly Arg Ile Ile Pro Gly Ala Asp Ala Asp Val Val Val<br>  390       395       400 | 1374 |
| tgg gac cca gaa gcc aca aag acc atc tca gcc agc acg cag gtc cag<br>Trp Asp Pro Glu Ala Thr Lys Thr Ile Ser Ala Ser Thr Gln Val Gln | 1422 |

```
                405                 410                 415                 420
gga gga gac ttc aac ctg tat gag aac atg cgc tgc cac ggc gtg cca                    1470
Gly Gly Asp Phe Asn Leu Tyr Glu Asn Met Arg Cys His Gly Val Pro
                        425                 430                 435 ctg gtc acc atc agc cgg ggg cgc gtc gtg tat gag aac ggc gtc ttc                    1518
Leu Val Thr Ile Ser Arg Gly Arg Val Val Tyr Glu Asn Gly Val Phe
            440                 445                 450 atg tgc gcc gag ggc acc ggc aag ttc tgt ccc ctg agg tcc ttc cca                    1566
Met Cys Ala Glu Gly Thr Gly Lys Phe Cys Pro Leu Arg Ser Phe Pro
                455                 460                 465 gac act gtc tac aag aag ctg gtc cag aga gag aag act tta aag gtt                    1614
Asp Thr Val Tyr Lys Lys Leu Val Gln Arg Glu Lys Thr Leu Lys Val
            470                 475                 480 aga gga gtg gac cgc act ccc tac ctg ggg gat gtc gct gtt gtc gtg                    1662
Arg Gly Val Asp Arg Thr Pro Tyr Leu Gly Asp Val Ala Val Val Val
485                 490                 495                 500 cac cct ggg aaa aaa gag atg gga acc cca ctc gca gac act cct acc                    1710
His Pro Gly Lys Lys Glu Met Gly Thr Pro Leu Ala Asp Thr Pro Thr
                505                 510                 515 cgg ccc gtc acc cgg cat ggg ggc atg agg gac ctt cac gaa tcc agc                    1758
Arg Pro Val Thr Arg His Gly Gly Met Arg Asp Leu His Glu Ser Ser
            520                 525                 530 ttc agc ctc tct ggc tct cag atc gat gac cat gtt cca aag cga gct                    1806
Phe Ser Leu Ser Gly Ser Gln Ile Asp Asp His Val Pro Lys Arg Ala
                535                 540                 545 tca gct cgg atc ctc gct cct ccc gga ggc agg tcg agt ggc att tgg                    1854
Ser Ala Arg Ile Leu Ala Pro Pro Gly Gly Arg Ser Ser Gly Ile Trp
            550                 555                 560 taaaggcatt gccaagcccc ccgagtgagg acgcaccgcc gccaccagcc cgcaactctc                  1914
cagccgaagc tgcaggggca ggagaggctg ggctgggtgg cacaccaccc gagggggggcc                 1974 ccgggaccca cggagccctc cctatgtctg caaagtgatt cactgtgctt cgagccaact                  2034
ctaacaggca ctttgagatg tgttcctcct gctgtagtcc tttctgcctt ggcctcggcg                  2094
ggcttttctg gggcccagga agcccacact atgcacagag cccaatgcat agagccctgg                  2154
ccagcccttc ctctcactcc tgcctccgct ggctttggga agcccagac tttagtgccc                   2214 tgcccctgg ctgactggcc agttgcccag agcactttag cagatgtggt ttcaaagtaa                   2274
aggcctcctc ccccacccct taggcccgt ggtgacattt cccaagtcag acagatgtca                   2334
gcttcccagc catgcccagg acgtcctatc tcccccaacc cacctctggc cctgtgtagg                  2394
ggcagggatg ggggtggctg ggactcctgg tgccccctcgc cagcttctcc tgcgccccgc                 2454
ccacaccctc ggggggggtca caggcccaga agggtagctg ggcggggctc gaggctggtg                 2514
ccaggcgcgt gtaaatggtt ttgttttgca cgtttggttt gcgcagtagt ttggtttgac                  2574
ttgtttgtgc atcctgtgaa aaataacggt gcttgtgtca ctagcataga atagcgacag                  2634
gaatagatgt ggtccttagg agacgctgca cttgacacca accagacagc acagggcagg                  2694
ggtggtggag ggggctgggc tcacaggcct ctcttttccc cgcctgcagt cttctgggct                  2754
gcgggaggcc ctggcccttt cccccttccc tccctccctt gtctagtttc ccacattcca                  2814
aaagggggcc tgggatgcta gccccagaga tgccagccct tcaggaagca ggtgtccttt                  2874 ccctctctg cccctgatca ctcccagcac tcccttgcc ttccctgtc ttcacctgcc                     2934 accacacaca cacacacaca cacacacaca cacacacgca tggcttccta taacttcttc                  2994
ctgctggaca gagactcagc gctcctcctg tgtgactggc aagaggcctc atgcctgctg                  3054
agagagggtc gacgcggccg                                                              3074
```

<210> SEQ ID NO 2
<211> LENGTH: 564
<212> TYPE: PRT
<213> ORGANISM: Homo sapiens

<400> SEQUENCE: 2

```
Met Leu Ala Asn Ser Ala Ser Val Arg Ile Leu Ile Lys Gly Gly Lys
1               5                   10                  15

Val Val Asn Asp Asp Cys Thr His Glu Ala Asp Val Tyr Ile Glu Asn
            20                  25                  30

Gly Ile Ile Gln Gln Val Gly Arg Glu Leu Met Ile Pro Gly Gly Ala
        35                  40                  45

Lys Val Ile Asp Ala Thr Gly Lys Leu Val Ile Pro Gly Gly Ile Asp
50                  55                  60

Thr Ser Thr His Phe His Gln Thr Phe Met Asn Ala Thr Cys Val Asp
65                  70                  75                  80

Asp Phe Tyr His Gly Thr Lys Ala Ala Leu Val Gly Gly Thr Thr Met
                85                  90                  95

Ile Ile Gly His Val Leu Pro Asp Lys Glu Thr Ser Leu Val Asp Ala
            100                 105                 110

Tyr Glu Lys Cys Arg Gly Leu Ala Asp Pro Lys Val Cys Cys Asp Tyr
        115                 120                 125

Ala Leu His Val Gly Ile Thr Trp Trp Ala Pro Lys Val Lys Ala Glu
130                 135                 140

Met Glu Thr Leu Val Arg Glu Lys Gly Val Asn Ser Phe Gln Met Phe
145                 150                 155                 160

Met Thr Tyr Lys Asp Leu Tyr Met Leu Arg Asp Ser Glu Leu Tyr Gln
                165                 170                 175

Val Leu His Ala Cys Lys Asp Ile Gly Ala Ile Ala Arg Val His Ala
            180                 185                 190

Glu Asn Gly Glu Leu Val Ala Glu Gly Ala Lys Glu Ala Leu Asp Leu
        195                 200                 205

Gly Ile Thr Gly Pro Glu Gly Ile Glu Ile Ser Arg Pro Glu Glu Leu
210                 215                 220

Glu Ala Glu Ala Thr His Arg Val Ile Thr Ile Ala Asn Arg Thr His
225                 230                 235                 240

Cys Pro Ile Tyr Leu Val Asn Val Ser Ser Ile Ser Ala Gly Asp Val
                245                 250                 255

Ile Ala Ala Ala Lys Met Gln Gly Lys Val Val Leu Ala Glu Thr Thr
            260                 265                 270

Thr Ala His Ala Thr Leu Thr Gly Leu His Tyr Tyr His Gln Asp Trp
        275                 280                 285

Ser His Ala Ala Ala Tyr Val Thr Val Pro Pro Leu Arg Leu Asp Thr
290                 295                 300

Asn Thr Ser Thr Tyr Leu Met Ser Leu Leu Ala Asn Asp Thr Leu Asn
305                 310                 315                 320

Ile Val Ala Ser Asp His Arg Pro Phe Thr Thr Lys Gln Lys Ala Met
                325                 330                 335

Gly Lys Glu Asp Phe Thr Lys Ile Pro His Gly Val Ser Gly Val Gln
            340                 345                 350

Asp Arg Met Ser Val Ile Trp Glu Arg Gly Val Val Gly Gly Lys Met
        355                 360                 365

Asp Glu Asn Arg Phe Val Ala Val Thr Ser Ser Asn Ala Ala Lys Leu
```

Leu Asn Leu Tyr Pro Arg Lys Gly Arg Ile Ile Pro Gly Ala Asp Ala
385                 390                 395                 400

Asp Val Val Trp Asp Pro Glu Ala Thr Lys Thr Ile Ser Ala Ser
            405                 410                 415

Thr Gln Val Gln Gly Gly Asp Phe Asn Leu Tyr Glu Asn Met Arg Cys
        420                 425                 430

His Gly Val Pro Leu Val Thr Ile Ser Arg Gly Arg Val Val Tyr Glu
        435                 440                 445

Asn Gly Val Phe Met Cys Ala Glu Gly Thr Gly Lys Phe Cys Pro Leu
    450                 455                 460

Arg Ser Phe Pro Asp Thr Val Tyr Lys Lys Leu Val Gln Arg Glu Lys
465                 470                 475                 480

Thr Leu Lys Val Arg Gly Val Asp Arg Thr Pro Tyr Leu Gly Asp Val
            485                 490                 495

Ala Val Val Val His Pro Gly Lys Lys Glu Met Gly Thr Pro Leu Ala
            500                 505                 510

Asp Thr Pro Thr Arg Pro Val Thr Arg His Gly Gly Met Arg Asp Leu
        515                 520                 525

His Glu Ser Ser Phe Ser Leu Ser Gly Ser Gln Ile Asp Asp His Val
        530                 535                 540

Pro Lys Arg Ala Ser Ala Arg Ile Leu Ala Pro Pro Gly Gly Arg Ser
545                 550                 555                 560

Ser Gly Ile Trp

<210> SEQ ID NO 3
<211> LENGTH: 1218
<212> TYPE: DNA
<213> ORGANISM: Homo sapiens

<400> SEQUENCE: 3

```
aggcattgcc aagcccccg agtgaggacg caccgccgcc accagcccgc aactctccag      60
ccgaagctgc aggggcagga gaggctgggc tgggtggcac accacccgag ggggccccg     120
ggacccacgg agccctccct atgtctgcaa agtgattcac tgtgcttcga gccaactcta    180
acaggcactt tgagatgtgt tcctcctgct gtagtccttt ctgccttggc ctcggcgggc    240
ttttctgggg cccaggaagc ccacactatg cacagagccc aatgcataga gccctggcca    300
gcccttcctc tcactcctgc ctccgctggc tttgggaaag cccagacttt agtgccctgc    360
cccctggctg actggccagt tgcccagagc actttagcag atgtggtttc aaagtaaagg    420
cctcctcccc cacccttag gccccgtggt gacatttccc aagtcagaca gatgtcagct    480
tcccagccat gccaggacg tcctatctcc cccaacccac ctctggccct gtgtaggggc    540
agggatgggg gtggctggga ctcctggtgc ccctcgccag cttctcctgc gccccgccca    600
caccctcggg ggggtcacag gcccagaagg gtagctgggc ggggctcgag ctggtgccca    660
ggcgcgtgta atggtttttg ttttgcacgt ttggtttgcg cagtagttg gtttgacttg    720
tttgtgcatc ctgtgaaaaa taacggtgct tgtgtcacta gcatagaata gcgacaggaa    780
tagatgtggt ccttaggaga cgctgcactt gacaccaacc agacagcaca gggcaggggt    840
ggtggagggg gctgggctca caggcctctc ttttccccgc ctgcagtctt ctgggctgcg    900
ggaggccctg gccctttccc cttccctcc cctccttgtc tagtttccca cattccaaaa    960
gggggcctgg gatgctagcc ccagagatgc cagcccttca ggaagcaggt gtcctttccc   1020
```

```
ctctctgccc ctgatcactc ccagcactcc ccttgccttc ccctgtcttc acctgccacc    1080
acacacacac acacacacac acacacacac acacgcatgg cttcctataa cttcttcctg    1140
ctggacagag actcagcgct cctcctgtgt gactggcaag aggcctcatg cctgctgaga    1200
gagggtcgac gcggccgc                                                  1218
```

<210> SEQ ID NO 4
<211> LENGTH: 20
<212> TYPE: PRT
<213> ORGANISM: Homo sapiens

<400> SEQUENCE: 4

```
Lys Glu Met Gly Thr Pro Leu Ala Asp Thr Pro Thr Arg Pro Val Thr
1               5                   10                  15

Arg His Gly Gly
            20
```